US00PP13136P2

(12) United States Plant Patent
Wilfret

(10) Patent No.: US PP13,136 P2
(45) Date of Patent: Oct. 29, 2002

(54) CALADIUM PLANT NAMED 'FLORIDA RED RUFFLES'

(75) Inventor: Gary J. Wilfret, Sarasota, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 60 days.

(21) Appl. No.: 09/865,883

(22) Filed: May 25, 2001

(51) Int. Cl.[7] ..... A01H 5/00

(52) U.S. Cl. ..... Plt./373
(58) Field of Search ..... Plt./373

*Primary Examiner*—Bruce R. Campell
*Assistant Examiner*—Anne Marie Grünberg

(57) ABSTRACT

A distinct cultivar of Caladium plant named 'Florida Red Ruffles', characterized by its compact and densely-foliated plant habit; upright, outwardly arching and symmetrical plant form; red and dark green bi-colored leaves that are lanceolate in shape with undulate margins that give the leaves a ruffled appearance; and tolerance to low temperatures and full sunlight conditions.

1 Drawing Sheet

BACKGROUND OF THE INVENTION

The present Invention relates to a new and distinct cultivar of Caladium plant, botanically known as *Caladium*× *hortulanum*, commercially referred to as lance-leaf Caladium, and hereinafter referred to by the cultivar name Florida Red Ruffles.

The new cultivar is a product of a planned and controlled breeding program conducted by the Inventor in Bradenton, Fla. The objective of the breeding program is to create densely-foliated compact Caladium cultivars with lanceolate-shaped leaves. The new cultivar originated from a cross-pollination made by the Inventor in 1982 of a proprietary lance-leaf Caladium selection identified as code number GC80-287, not patented, as the female, or seed, parent with the Caladium cultivar Red Frill, not patented, as the male, or pollen, parent. The cultivar Florida Red Ruffles was discovered and selected by the Inventor as a plant within the progeny of the stated cross-pollination in a controlled environment in Bradenton, Fla., in 1985.

Asexual propagation of the new cultivar by tuber divisions since 1985, in Bradenton, Fla., has shown that the unique features of this new Caladium plant are stable and reproduced true to type in successive generations of asexual propagation.

SUMMARY OF THE INVENTION

The new Caladium has not been observed under all possible environmental conditions. The phenotype may vary somewhat with variations in environment such as temperature, light intensity, fertilizer rate and type, and water status, without, however, any variance in genotype.

The following traits have been repeatedly observed and are determined to be the unique characteristics of 'Florida Red Ruffles'. These characteristics in combination distinguish 'Florida Red Ruffles' as a new and distinct cultivar:

1. Compact and densely-foliated plant habit.

2. Upright, outwardly arching and symmetrical plant form.

3. Red and dark green bi-colored leaves that are lanceolate in shape with undulate margins that give the leaves a ruffled appearance.

4. Compared to other known Caladium cultivars, relatively tolerant to low temperatures.

5. Tolerant to full sunlight conditions.

When grown in side-side comparisons in Bradenton, Fla., plants of the new Caladium differ from plants of the female parent, the selection GC80-287, primarily in leaf color. Plants of the new Caladium have red and dark green bi-colored leaves whereas plants of the selection GC80-287 have green-colored leaves with red-colored veins and white-colored interveinal areas.

Plants of the new Caladium are most similar to plants of the male parent, the cultivar Red Frill. However, when grown in side-side comparisons in Bradenton, Fla., plants of the new Caladium differ from plants of the cultivar Red Frill in the following characteristics:

1. Plants of the new Caladium are more compact and not as open as plants of the cultivar Red Frill.

2. Plants of the new Caladium have broader leaves than plants of the cultivar Red Frill.

3. Leaves of plants of the new Caladium have undulate margins giving a ruffled appearance to the leaves whereas leaves of plants of the cultivar Red Frill have smooth margins and leaves are not ruffled in appearance.

4. Plants of the new Caladium have stronger petioles than plants of the cultivar Red Frill.

5. Plants of the new Caladium are more low temperature tolerant than plants of the cultivar Red Frill.

Plants of the new Caladium can also be compared to plants of the cultivar Rosalie, not patented. When grown in side-side comparisons in Bradenton, Fla., plants of the new Caladium differ from plants of the cultivar Rosalie in the following characteristics:

1. Plants of the new Caladium are much more compact, shorter, and not as open as plants of the cultivar Rosalie.

2. Plants of the new Caladium are more densely foliated than plants of the cultivar Rosalie.

3. Leaves of plants of the new Caladium have undulate margins giving a ruffled appearance to the leaves whereas leaves of plants of the cultivar Rosalie have smooth margins and leaves are not ruffled in appearance.

4. Plants of the new Caladium have much stronger petioles than plants of the cultivar Rosalie.

5. Plants of the new Caladium are more low temperature tolerant than plants of the cultivar Rosalie.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Caladium. The photograph comprises a side perspective view of a typical 7-week old plant of 'Florida Red Ruffles'.

DETAILED BOTANICAL DESCRIPTION

The following observations, measurements and comparisons describe 7-week old plants (from planting a tuber division) grown in Bradenton, Fla., during the summer in a shaded glass-covered greenhouse and under commercial production conditions in 15-cm containers. During the production of the plants, day temperatures ranged from 32 to 35° C., night temperatures ranged from 18 to 21° C., and light levels were about 5,000 to 6,000 foot-candles.

In the following description, color references are made to The Royal Horticultural Society Colour Chart except where general terms of ordinary dictionary significance are used.

Botanical classification: *Caladium×hortulanum* cultivar Florida Red Ruffles.

Parentage:

*Female parent.*—Proprietary *Caladium×hortulanum* selection identified as GC80-287, not patented.

*Male parent.*—*Caladium×hortulanum* cultivar Red Frill, not patented.

Propagation:

*Type.*—By tuber divisions.

*Tuber description.*—Number of dominant buds per tuber: About 6 to 8. Diameter: About 3.8 to 6.4 cm. Color: Epidermis, 199A; interior, 10A.

*Time to initiate roots on a tuber division.*—About 8 days at 26.7° C.

*Time to produce a fully rooted tuber division.*—About 23 days at 26.7° C.

*Root description.*—Dense, thick and white to pink in color.

Plant description:

*Plant habit.*—Compact and densely-foliated.

*Plant form.*—Upright, outwardly arching and symmetrical plant habit.

*Growth habit.*—Mostly erect when leaves are developing, becoming outwardly arching as leaves develop. Plants of the new Caladium are typically grown in 10 to 15-cm containers.

*Plant height.*—About 28 cm from soil level to top of leaf plane.

*Plant spread.*—About 43 cm.

*Growth rate.*—Rapid growth rate; first leaf opens about 23 days after planting; about 7 weeks are required to produce a finished plant in 15-cm container from a division.

*Foliage description.*—Quantity: About 27 per plant. Length: About 20.8 cm. Width: About 15.3 cm. Shape: Lanceolate. Apex: Elongated acuminate. Base: Obtuse to cordate. Margin: Entire, undulate giving a ruffled appearance to the leaf. Aspect: Initially upright, then outwardly arching; concave. Texture, both surfaces: Smooth, glabrous, durable and flexible. Venation pattern: Penniform. Color: Upper surface: Center, red, 47A; margin, dark green, 147A, about 5 mm in width; venation, same or slightly darker than lamina colors. Lower surface: 181C; venation, same as lamina color. Petiole: Aspect: Mostly erect with slight outward bend at leaf attachment. Length: About 28 cm. Diameter: About 9 mm. Strength: Strong. Color: 199D with 4 to 5 darker brown, 200C, longitudinal stripes, about 0.4 mm in width, and a few elongated dark brown, 200C, speckles.

*Flower description.*—Flower development has not been observed on plants of the new Caladium.

Disease/pest resistance: Plants of the new Caladium have not been observed to be resistant to pathogens or pests common to Caladium.

Temperature/weather tolerance: Plants of the new Caladium have been observed to be tolerant to temperatures as low as 5° C. and as high as 38° C. Plants of the new Caladium have been observed to be tolerant to rain, wind and full sunlight conditions.

It is claimed:

1. A new and distinct cultivar of Caladium plant named 'Florida Red Ruffles', as illustrated and described.

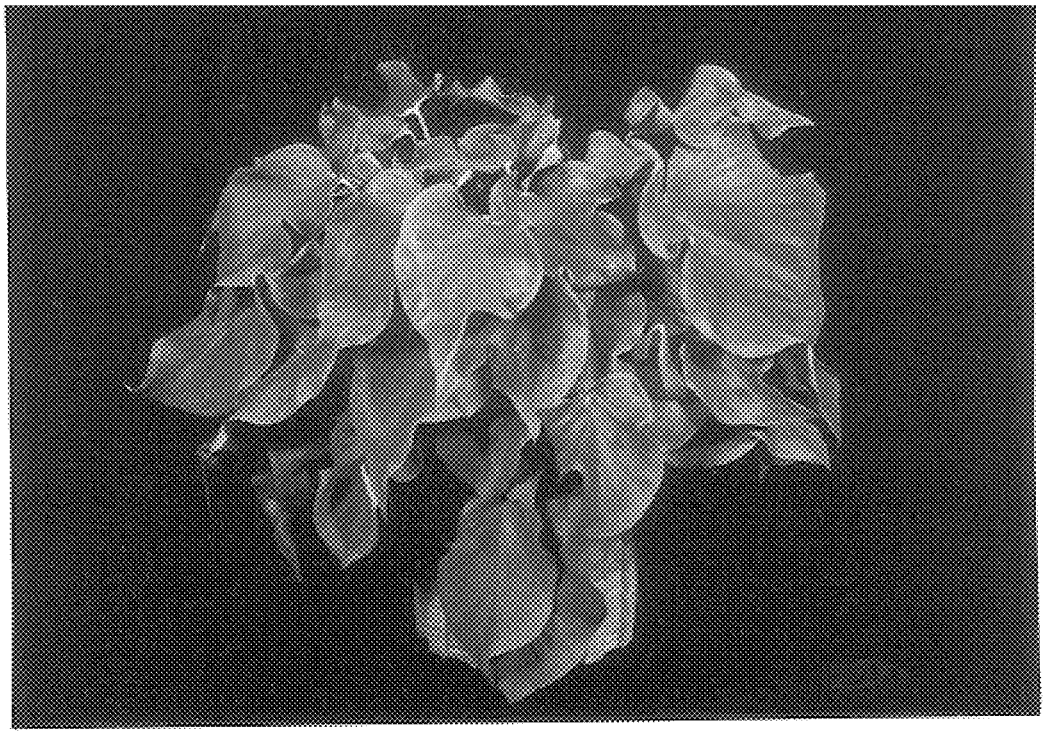

* * * * *